US007641860B2

(12) United States Patent
Matteo

(10) Patent No.: US 7,641,860 B2
(45) Date of Patent: Jan. 5, 2010

(54) MODULAR AND RECONFIGURABLE MULTI-STAGE MICROREACTOR CARTRIDGE APPARATUS

(75) Inventor: Joseph C. Matteo, Walland, TN (US)

(73) Assignee: NanoTek, LLC, Louisville, TN (US)

( * ) Notice: Subject to any disclaimer, the term of this patent is extended or adjusted under 35 U.S.C. 154(b) by 201 days.

(21) Appl. No.: 11/421,678

(22) Filed: Jun. 1, 2006

(65) Prior Publication Data

US 2007/0280855 A1 Dec. 6, 2007

(51) Int. Cl.
*B01J 10/00* (2006.01)
*B01L 9/00* (2006.01)
*C12M 1/00* (2006.01)

(52) U.S. Cl. ....................... 422/100; 422/104; 422/129; 435/289.1

(58) Field of Classification Search ....................... None
See application file for complete search history.

(56) References Cited

U.S. PATENT DOCUMENTS 4,670,404 A 6/1987 Swift et al.
5,387,397 A 2/1995 Strauss et al.
5,614,154 A 3/1997 Glatz et al. ................. 422/103
5,808,020 A 9/1998 Ferrieri et al.
5,842,787 A 12/1998 Kopf-Sill et al.
5,856,671 A * 1/1999 Henion et al. ............... 250/288
5,858,187 A 1/1999 Ramsey
5,859,070 A 1/1999 Jackson
5,921,678 A 7/1999 Desai et al.
5,922,591 A 7/1999 Anderson et al.
5,961,932 A 10/1999 Ghosh et al.
5,965,092 A 10/1999 Chatterjee et al.
5,976,472 A 11/1999 Chatterjee et al.

(Continued)

FOREIGN PATENT DOCUMENTS

DE 10 2005 025 499 12/2006

(Continued)

OTHER PUBLICATIONS

J. Michael Ramsey, Chemistry and Chemical Analysis on Microfabricated Devices, Chemical and Analytical Sciences Division, Jan. 28, 2004, Oak Ridge, Tennessee.

(Continued)

*Primary Examiner*—Jill Warden
*Assistant Examiner*—Timothy G Kingan
(74) *Attorney, Agent, or Firm*—Fish & Richardson P.C.

(57) ABSTRACT

A modular and reconfigurable multi-stage microreactor cartridge apparatus provides a manifold for removably attaching multiple microfluidic components such as microreactors. The microfluidic components are attached at microfluidic component ports having two input/output terminals, which microfluidic component ports are connected via connections internal to the manifold to other microfluidic component ports providing a microfluidic circuit. The microfluidic component may be a microfluidic circuit plug-in or a cartridge having a mounting block with two input/output terminals and a fastener aperture and fluidic tubing having a first and second transport portion and a body portion, the three portions being disposed in substantially parallel planes and the body portion being would in a coil around a spool. The coil is connected to the mounting block by either epoxy protector or L-bracket. The cartridge has a first and a second remote input/output terminal connected to the first and second transport lines respectively.

22 Claims, 10 Drawing Sheets

U.S. PATENT DOCUMENTS

| | | | |
|---|---|---|---|
| 6,001,229 A | 12/1999 | Ramsey | |
| 6,010,607 A | 1/2000 | Ramsey | |
| 6,033,546 A | 3/2000 | Ramsey | |
| 6,036,927 A | 3/2000 | Chatterjee et al. | |
| 6,062,261 A | 5/2000 | Jacobson et al. | |
| 6,106,710 A | 8/2000 | Fischer et al. | |
| 6,110,343 A | 8/2000 | Ramsey et al. | |
| 6,117,396 A | 9/2000 | Demers | 422/100 |
| 6,120,666 A | 9/2000 | Jacobson et al. | |
| 6,139,734 A | 10/2000 | Settlage et al. | |
| 6,180,372 B1 | 1/2001 | Franzen | |
| 6,187,206 B1 | 2/2001 | Bernier et al. | |
| 6,231,737 B1 | 5/2001 | Ramsey et al. | |
| 6,235,471 B1 | 5/2001 | Knapp et al. | |
| 6,241,953 B1 | 6/2001 | Krijgsman | |
| 6,284,525 B1 | 9/2001 | Mathies et al. | |
| 6,315,905 B1 | 11/2001 | Settlage et al. | |
| 6,319,476 B1 | 11/2001 | Victor, Jr. et al. | 422/103 |
| 6,342,142 B1 | 1/2002 | Ramsey | |
| 6,376,181 B2 | 4/2002 | Ramsey et al. | |
| 6,409,072 B1 | 6/2002 | Breuer et al. | |
| 6,440,669 B1 | 8/2002 | Bass et al. | |
| 6,444,461 B1 | 9/2002 | Knapp et al. | |
| 6,475,363 B1 | 11/2002 | Ramsey | |
| 6,485,692 B1 | 11/2002 | Freitag et al. | |
| 6,524,456 B1 | 2/2003 | Ramsey et al. | |
| 6,537,506 B1 | 3/2003 | Schwalbe et al. | |
| 6,541,274 B2 | 4/2003 | Nagle et al. | |
| 6,572,830 B1 | 6/2003 | Burdon et al. | |
| 6,620,386 B1 | 9/2003 | Welch | |
| 6,632,656 B1 | 10/2003 | Thomas et al. | |
| 6,706,538 B1 | 3/2004 | Karg et al. | 436/180 |
| 6,749,814 B1 | 6/2004 | Bergh et al. | |
| 6,806,087 B2 | 10/2004 | Kibby et al. | |
| 6,818,189 B1 | 11/2004 | Adris et al. | |
| 6,828,143 B1 * | 12/2004 | Bard | 506/15 |
| 6,858,435 B2 | 2/2005 | Chervet et al. | |
| 6,890,493 B1 | 5/2005 | Bergh et al. | |
| 6,896,855 B1 | 5/2005 | Kohler et al. | |
| 6,926,313 B1 | 8/2005 | Renzi | 285/353 |
| 6,958,122 B1 | 10/2005 | Gidner et al. | |
| 6,977,064 B1 | 12/2005 | Adris et al. | |
| 7,182,371 B1 | 2/2007 | Renzi | 285/124.1 |
| 7,244,961 B2 | 7/2007 | Jovanovich et al. | |
| 2004/0022696 A1 | 2/2004 | Zigler et al. | |
| 2004/0208794 A1 | 10/2004 | Karg et al. | 422/100 |
| 2004/0258615 A1 | 12/2004 | Buchanan et al. | |
| 2005/0019213 A1 | 1/2005 | Kechagia et al. | |
| 2005/0052509 A1 | 3/2005 | Gilligan et al. | |
| 2005/0181519 A1 | 8/2005 | Karg et al. | 436/180 |
| 2005/0221373 A1 | 10/2005 | Enzelberger et al. | |
| 2005/0226776 A1 | 10/2005 | Brady et al. | |
| 2005/0232387 A1 | 10/2005 | Padgett et al. | |
| 2006/0150385 A1 | 7/2006 | Gilligan et al. | |
| 2006/0289737 A1 | 12/2006 | Bassmann et al. | |
| 2007/0071664 A1 | 3/2007 | Bellos et al. | |

FOREIGN PATENT DOCUMENTS

| | | |
|---|---|---|
| JP | 9-263591 | 10/1997 |
| JP | 2000-249694 | 9/2000 |
| JP | 2005065632 | 3/2005 |
| PL | 0264094 | 9/1988 |
| WO | WO 99/67656 | 12/1999 |
| WO | WO 01/34660 | 5/2001 |
| WO | WO 02/11880 | 2/2002 |
| WO | WO 03/002157 | 1/2003 |
| WO | WO 03/002489 | 1/2003 |
| WO | 03078358 | 9/2003 |
| WO | 2005056872 | 6/2005 |
| WO | 2005082535 | 9/2005 |

OTHER PUBLICATIONS

Sheila H. Dewitt, Microreactors for Chemical Synthesis, Chemical Biology, 1999, 350-356.
Stephen J. Haswell, The Application of Micro Reactors to Synthetic Chemistry, The Royal Society of Chemistry, Feb. 5, 2001, 391-398.
Ann M. Thayer, Harnessing Microreactions, Chemical and Engineering News, May 30, 2005, pp. 43-52, vol. 83. No. 22.
Notification of Transmittal of the International Search Report and the Written Opinion of the International Searching Authority, or the Declaration, PCT/US07/70218, 8 pages, Nov. 18, 2008.
Advion, Triversa for Metabolite Identification, (2 pages).
Amin et al., "Peak Parking Technique for the Simultaneous Determination of Anions and Cations", Anal Bioanal Chem. 381:1426-1431, 2005.
Bodnar et al., "Exploiting the Complementary Nature of LC/MALDI/MS/MS and LC/ESI/MS/MS for Increased Proteome Coverage", J Am Soc Mass Spectrom 14:971-979, 2003.
Davis et al., "Low Flow High-Performance Liquid Chromatography Solvent Delivery System Designed for Tandem Capillary Liquid Chromatography-Mass Spectrometry", J Am Soc Mass Spectrom 6:571-577, 1995.
Davis et al., "Variable Flow Liquid Chromatography-Tandem Mass Spectrometry and the Comprehensive Analysis of Complex Protein Digest Mixtures", J Am Soc Mass Spectrom 8:1059-1069, 1997.
Dionex, Probot Microfraction Collector, (4 pages).
Eksigent, "The Eksigent NanoLC System for Proteomics", www.eksigent.com, (5 pages).
Geromanos et al., "Tuning of an Electrospray Ionization Source for Maximum Peptide-Ion Transmission into a Mass Spectrometer", Anal. Chem. 72:777-790, 2000.
Gillies et al., J. Label. Compds. Radiopharm., 42, (1999) S886-S888.
Goodlett et al., "Proteomics Without Polyacrylamide: Qualitative and Quantitative Uses of Tandem Mass Spectrometry in Proteome Analysis", Funct Integr Genomics 2:138-153, 2002.
Hadd et al., "Microchip Device for Performing Enzyme Assays," Anal. Chem. 1997, 67, 3407-3412.
Haswell et al., "Chemical and Biochemical Microreactors," The Royal Society of Chemistry 2001, *Chem. Comm.* 2001, 391-398.
Jensen, "The Impact of MEMS on the Chemical and Pharmaceutical Industries," Solid-State Sensor and Actuator Workshop, So. Carolina, Jun. 4-8, 2000, 105-110.
Kammerer et al., "Achiral-chiral LC/LC—MS/MS Coupling for Determination of Chiral Discrimination Effects in Phenprocoumon Metabolism", Anal. Biochem. 339:297-309, 2005.
LC Packings, From the Leaders in Capillary LC, "LC/MS Tools", www:lcpakings.com, (16 pages).
Lin et al., "Peak Parking Using a Finnigan™ LCQ™ Deca", Thermo Electron Corporation, PSB 107, (2 pages).
Liu et al., "Enzyme Conformational Dynamics During Catalysis and in the 'Resting State' Monitored by Hydrogen/Deuterium Exchange Mass Spectrometry", FEBS Letters 580:5137-5142, 2006.
Lu et al., "A New Approach for Sequencing Human IRS1 Phosphotyrosine-Containing Peptides Using CapLC-Q-TOF$^{micro}$", J Mass Spectrometry 40:599-607, 2005.
Lund et al., "Comparison of Peak Parking Versus Automated Fraction Analysis of a Complex Protein Mixture", Waters, PosterREPRINT, (6 pages).
Martin et al., "Subfemtomole MS and MS/MS Peptide Sequence Analysis Using Nano-HPLC Micro-ESI Fourier Transform Ion Cyclotron Resonance Mass Spectrometry", Anal. Chem. 72:4266-4274, 2000.
Miyabe et al., "A Kinetic Parameter Concerning Mass Transfer in Silica Monolithic and Particulate Stationary Phases Measured by the Peak-Parking and Slow-Elution Methods", J. Sep. Sci. 29:2452-2462, 2006.
Okamoto et al., "On-line Sample Enrichment System Coupled to Electrospray Ionization Time-of-Flight Mass Spectrometry (ESI-TOF-MS)", J of Pharmaceutical and Biomedical Analysis 41:707-713, 2006.

Opiteck et al., "Comprehensive On-Line LC/LC/MS of Proteins", Anal. Chem. 69:1518-1524, 1997.
Pan et al., "Folding Kinetics of the S100A11 Protein Dimer Studied by Time-Resolved Electrospray Mass Spectrometry and Pulsed Hydrogen-Deuterium Exchange", Biochemistry 45:3005-3013, 2006.
Patterson et al., "Interfacing Capillary/Nano LC with MALDI/MS for High-Throughput Proteonmics", LC Packings, (1 page).
Prolexys Pharmaceuticals, Inc., "HySpec", (2 pages).
Staack et al., "The Combination of Liquid Chromatography/Tandem Mass Spectrometry and Chip-Based Infusion for Improved Screening and Characterization of Drug Metabolites", Rapid Commun. Mass Spectrom. 19:618-626, 2005.
Strittmatter et al., "Proteome Analyses Using Accurate Mass and Elution Time Peptide Tags with Capillary LC Time-of-Flight Mass Spectrometry", J Am Soc Mass Spectrom 14:980-991, 2003.
Vissers et al., "A Novel Interface for Variable Flow Nanoscale LC/MS/MS for Improved Proteome Coverage", J Am Soc Mass Spectrom 13:760-771, 2002.
Washburn et al., "Large-scale Analysis of the Yeast Proteome by Multidimensional Protein Identification Technology", Nature Biotechnology, hhtp://biotech.nature.com, 19:242-247, 2001.
Wilm et al., "Analytical Properties of the Nanoelectrospray Ion Source", Analytical Chemistry 68:1-8, 1996.
Zeller et al., "the Impact of Chromatography and Mass Spectrometry on the Analysis of Protein Phosphorylation Sites", Anal Bioannal Chem 378:898-909, 2004.
Zhou et al., "Quasi-linear Gradients for Capillary Liquid Chromatography with Mass and Tandem Mass Spectrometry", Rapid Commun. Mass Spectrom 14:432-438, 2000.

* cited by examiner

MODULAR AND RECONFIGURABLE MULTI-STAGE MICROREACTOR CARTRIDGE APPARATUS

FIELD

The present invention relates to the field of microfluidic chemical reactions and analyses of the same. More particularly, it relates to a modular and reconfigurable multi-stage microreactor cartridge apparatus.

BACKGROUND AND SUMMARY

Microfluidics have been used to manipulate fluids in channels with height and width that typically range from 1 to 500 micrometers. Fluids are moved in volumes of nanoliters or microliters. "Lab-on-a-chip" technology has used microfluidics to perform chemical reactions and analyses at very high speeds while consuming small amounts of starting materials. Various chemical reactions require difficult conditions such as high pressure and high temperatures. Microfluidic systems use miniaturized reactors, mixers, heat exchangers, and other processing elements for performing chemical reactions on a miniature scale. Such systems are useful for reactions such as pharmaceutical or laboratory reactions where very small and accurate amounts of chemicals are necessary to successfully arrive at a desired product. Furthermore, use of microfluidic systems increases efficiency by reducing diffusion times and the need for excess reagents.

Applications for microfluidic systems are generally broad, but commercial success has been slow to develop in part because microfluidic devices are difficult and costly to produce. Another significant hurdle in microfluidics is addressing the macroscale to microscale interface. Other considerable problems include clogging of the systems and accumulations of air bubbles that interfere with proper microfluidic system operation. Thus, there is a need for a low cost solution for microfluidic systems. Preferably, but not necessarily, such solution would allow easy replacement of microfluidic components of various types in order to build microfluidic systems and circuits to suit the needs of a particular application such as providing the specific circuit necessary to produce a particular product.

A cartridge system having a manifold with at least one microfluidic component port with at least two input/output terminals for connecting at least one microfluidic component, and a connection block with a system input and a system output is disclosed. A microfluidic component that may be removably attached to the cartridge system is a capillary plug-in, also known as a cartridge, which has a mounting area with at least first and second component input/output terminals and a fastener aperture, fluidic tubing having first and second transport and body portions, and a fastener. The first transport portion is connected to the first component input/output terminal of the mounting block, and the second transport portion is connected to the second component input/output terminal of the mounting area. The first and second transport and body portions are preferably disposed in substantially the parallel planes. Alternatively, the first and second transport portions may be disposed substantially in parallel planes with the body portion disposed in planes substantially perpendicular to the first and second transport portions.

The cartridge system may have several microfluidic component ports with several microfluidic components removably attached thereto. One or more of the microfluidic components may be a microfluidic circuit plug-in, and one or more of the microfluidic components may be a capillary plug-in or a cartridge. Further, input and output fittings can be integrated in a common manifold or in a separate connector block (eg block 32)

The fluidic tubing of the capillary plug-in or cartridge is preferably microfluidic tubing, but may also be small bore tubing and may be composed of glass or plastic. The first transport portion is connected to the body portion, which is connected to the second transport portion. Preferably, the body portion is wound in a coil shape around or inside a spool. Furthermore, the cartridge may have one or two w-rings or other high pressure seals disposed at the first or second input/output terminals for providing a seal between the first or second input/output terminals and the microfluidic component port of the cartridge system when the cartridge is used in a cartridge system.

BRIEF DESCRIPTION OF THE DRAWINGS

The preferred embodiments of the invention will now be described in further detail with reference to the drawings wherein like reference characters designate like or similar elements throughout the several drawings as follows:

FIG. 2 is an overhead view of the cartridge system with a connection block, three capillary plug-ins, and a microfluidic circuit plug-in.

FIG. 4 is a view of a microfluidic circuit plug-in.

FIG. 5 is a view of a capillary plug-in.

FIG. 6 is a side view of a capillary plug-in.

FIG. 7 is a cross-sectional view of the capillary plug-in.

FIG. 9 is a cross-sectional view of the cartridge system of FIG. 8 and a capillary plug-in.

DETAILED DESCRIPTION

The present disclosure provides a modular and reconfigurable multi-stage microreactor cartridge apparatus, referred to as a cartridge system. Some of the challenges associated with microfluidics include increasing the speed of microfluidic reaction processes and reducing the amount of dead space associated with microfluidic systems. The cartridge system addresses these and other concerns by use of an assembly of individual microfluidic flow reactors attached to a manifold cartridge enabling quick, low dead volume connections and reconfiguring of the system to support different process steps and applications. This is accomplished because of the close proximity of the multiple reactors in the cartridge system. Other problems associated with microfluidics include removal from the system of unwanted waste and residue while minimizing the amount of costly reagent lost, designing a low-cost method of repeatedly inputting reagent into a system as it is used, or replacing unnecessary microreactor devices with different devices necessary for a new application of the cartridge system. Another problem is lack of access to intermediate products in a multi-stage micro-fluidic reactor. These problems are solved by utilizing cartridge system manifold connections that provide the ability to input reactants or dispense products at various points in the microfluidic process.

Figure 1:
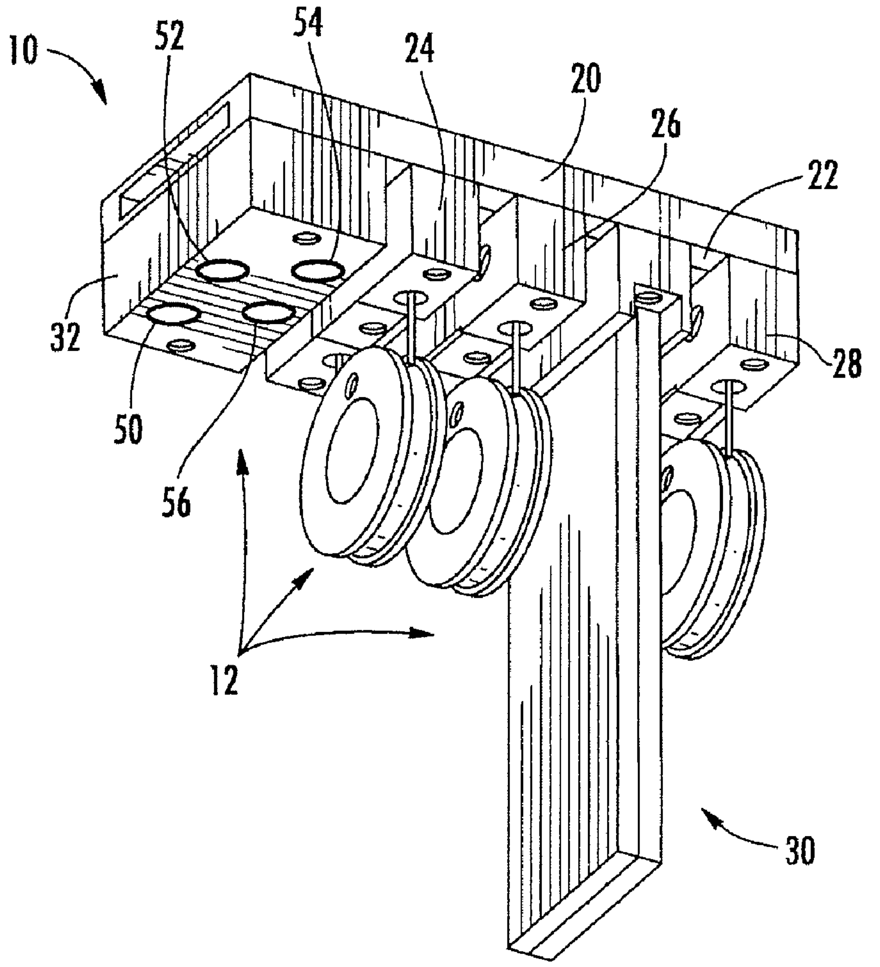
FIG. 1 is a component port-side view of the cartridge system with a connection block, a first cartridge, a second cartridge, a microfluidic circuit plug-in, and a third cartridge.
Figure 2:
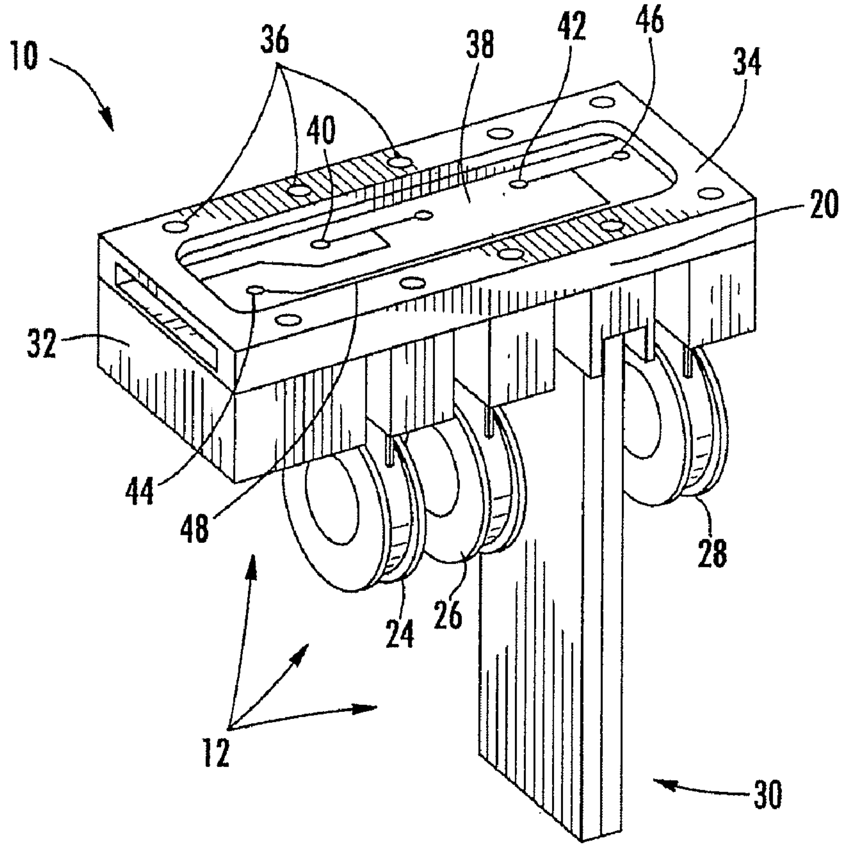

Referring now to FIG. 1, the cartridge system 10 is shown from underneath. The manifold 20 of the cartridge system 10 serves several functions, including its use as a connector for microfluidic components. In one embodiment, the manifold 20 is rectangular including two relatively large surfaces: a lower surface 22 and an upper surface 34, which is shown in FIG. 2. Several microfluidic components 12 may be removably attached to the lower surface 22 of the manifold 20. The microfluidic components 12 may be capillary plug-ins, 24, 26, and 28, which are a type of cartridge, microfluidic circuit plug-ins 30, and/or connection blocks 32. Cartridges, capillary plug-ins 24, 26, and 28 and microfluidic circuit plug-ins 30 can perform a variety of functions including, but not limited to, supplying reagent and serving as a type of reactor providing the ability to combine multiple reagents and supply heat or remove heat as necessary for the reaction being performed. Such a supply or drain of heat may be provided by an outside source connected to or surrounding the capillary plug-ins 24, 26, and 28 and the microfluidic circuit plug-ins 30.

Connection block 32 has several terminals, 50, 52, 54, and 56, which are used for connecting the cartridge system 10 to external devices. In one embodiment, terminal 50 is an input terminal for inputting fluid or reagent, terminal 52 is connected to a point somewhere within the cartridge system 10 for remotely flushing waste from a component 12, or for dispensing intermediate product for testing or other purposes. Terminal 54 is connected to another point somewhere within the cartridge system 10 for remotely filling a component 12 with reagent, and terminal 56 is connected to the output of the system. All of the terminals 50, 52, 54, and 56 could be utilized differently than the example above in other embodiments.

The upper surface 34 of the manifold 20 is shown in FIG. 2, which is a view of the cartridge system 10 from above. From this view, the manifold fastener apertures 36 are visible along the sides of the upper surface 34 of the manifold 20. As shown, two manifold fastener apertures 36 are provided for each microfluidic component 24, 26, 30, and 28, formed on the upper surface 34. Two manifold fastener apertures 36 are also provided for connection to block 32. Slightly recessed from the upper surface 34 of the manifold 20 is the trace surface 38. The trace surface 38 includes several nodes 40, 42, 44, and 46, and traces 48, which represent the fluidic connections internal to the manifold 20. The trace lines 48 and nodes 40 provide the user with a representation of the connections internal to the manifold 20.

Figure 4:
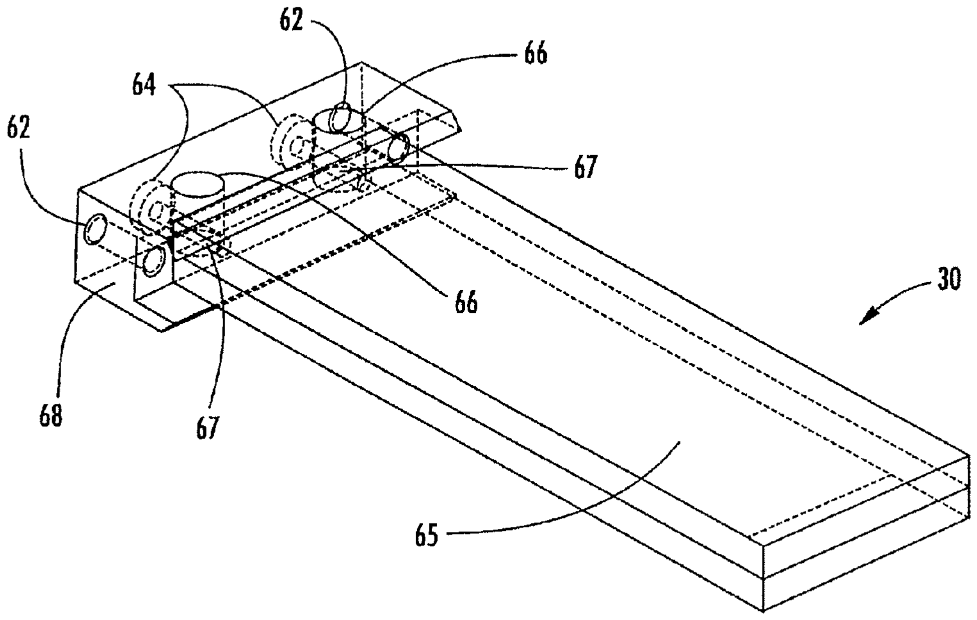
Figure 5:
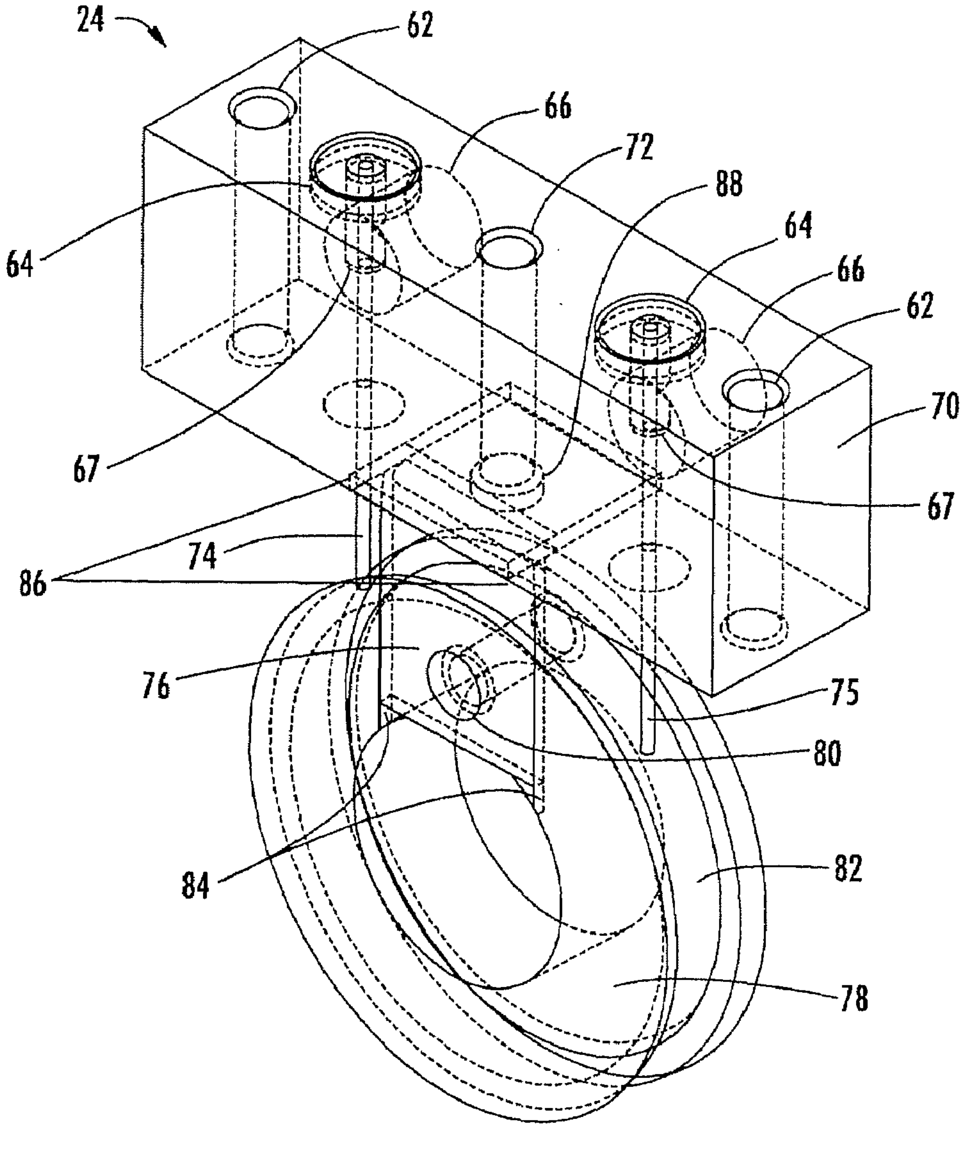

At various points within the cartridge system, waste (or intermediate products) may be remotely expelled and reagent supplies may be remotely refilled by way of remote input/output terminals 66, located on capillary plug-ins 24 and microfluidic circuit plug-ins 30 (as shown in FIGS. 4 and 5). For example, if capillary plug-in 24 contained a reagent supply depleted through use, node 40 (FIG. 2) represents a connection internal to the manifold 20 between the connection block 32 and an input/output terminal of capillary plug-in 24. Therefore, a new reagent supply could be input through connection block 32. Similarly, if microfluidic circuit plug-in 30 required cleansing, node 42 represents an internal connection between the connection block 32 and the microfluidic circuit plug-in 30 input/output terminal 64 (FIG. 4). Thus, the manifold 20 could be configured for remote waste removal by pumping solvent through microfluidic circuit plug-in 30. The trace 48 and node 40, 42, 44, and 46 configuration shown in FIG. 2 is included for illustrative purposes, and it should be understood that numerous internal connection configurations could be used in order to maximize the effectiveness of a cartridge system for a particular application. For example, if it is known that microfluidic components would require frequent refilling, then microfluidic components having remote input/output terminals or manifolds with suitable connections should be used.

In one embodiment node 44, on the left-hand side of the trace surface 38, is connected to nodes 42 and 46 as shown by trace line 48. Node 44 represents an internal connection to block 32 attached to the bottom surface 22 of the manifold 20. Thus, a port on connection block 32, such as port 54, discussed above and shown on FIG. 1, could be represented by node 44, which is connected to nodes 42 and 46 by trace line 48. In this embodiment, nodes 44, 42, and 46 represent connections to port 54 of the connection block 32. Nodes 42 and 44 are connected to microfluidic circuit plug-in 30 and capillary plug-in 28 respectively. Therefore, one reagent supply could simultaneously refill multiple fluidic components 12 secured to the manifold 20 as represented by nodes 42 and 46—in this example components 30 and 28.

Figure 3:
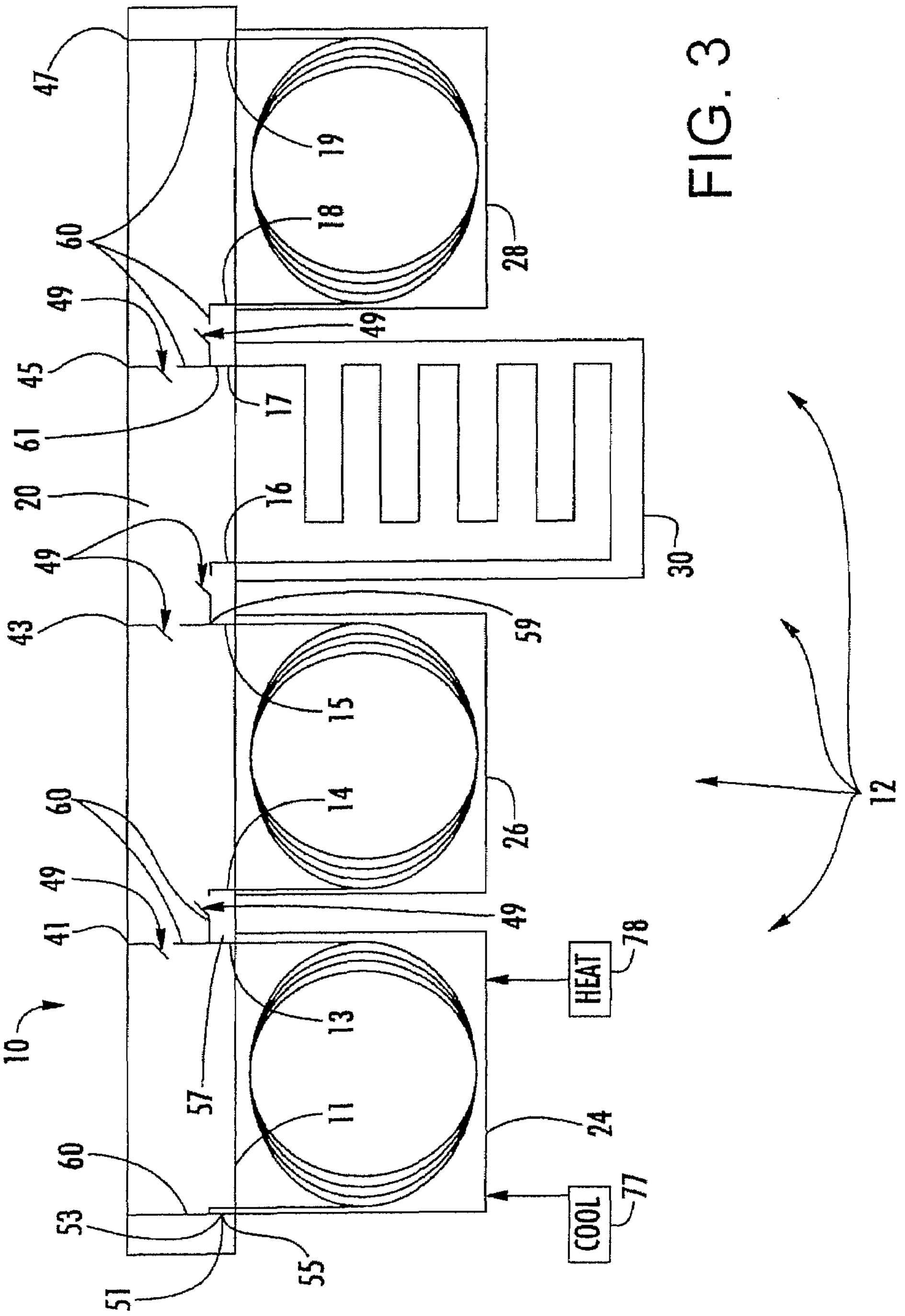
FIG. 3 is a schematic view of the cartridge system showing the internal connections of the system.

FIG. 3 is a schematic diagram of the cartridge system 10. The purpose of this figure is to demonstrate the relationship among the various fluidic components 12 when they are attached to the manifold 20 by showing the fluidic connections 60 formed inside the manifold 20. The manifold 20 is represented by the rectangle at the top of the figure. The inputs 51 and 53 of the cartridge system 10 are shown on the left-hand side of the manifold 20 by arrows. Input 51 may be connection block terminal 50, 52, 54, or 56 (FIG. 1). Similarly, input 53 may be connection block terminal 50, 52, 54, or 56. In one embodiment input 51 and input 53 are the same connection block terminal 50, 52, 54, or 56 (FIG. 1). Inputs 51 and 53 intersect at fluidic junction 55, which is also connected to capillary plug-in 24 at manifold terminal 11. In typical use, the fluids from inputs 51 and 53 combine at their junction and flows into the capillary plug in 24, where they typically react.

Capillary plug-in 24 is connected to fluidic junction 57 at manifold terminal 13; and fluidic junction 57 is also connected to input/output 41 and capillary plug-in 26 at manifold terminal 14. In one embodiment, fluidic junction 57 may include a switch 49 for allowing or blocking fluid flow entering or exiting fluidic junction 57. Input/output 41 may be connection block terminal 50, 52, 54, or 56 (FIG. 1). Capillary plug-in 26 is connected to fluidic junction 59 at manifold terminal 15 and fluidic junction 59 may have a switch 49 for allowing or blocking fluid flow entering or exiting fluidic junction 59. Fluidic junction 59 is connected to input/output 43 and microfluidic circuit plug-in 30 at manifold terminal 16. Likewise microfluidic circuit plug-in 30 is connected to fluidic junction 61 at manifold terminal 17. Fluidic junction 61 may have a switch 49 for allowing or blocking fluid flow entering or exiting fluidic junction 61, and fluidic junction 61 is connected to input/output 45 and capillary plug-in 28 at manifold terminal 18. Capillary plug-in 28 is connected to output 47 at manifold terminal 19. Output 47 may be connection block terminal 50, 52, 54, or 56 (FIG. 1). In other embodiments, the fluidic components 12 can be arranged in various combinations and in different orders than that shown in FIG. 3. For example, two capillary plug-ins 24 and 26 and two microfluidic circuit plug-ins 30 could be used. Manifold terminals 11, 13, 14, 15, 16, 17, 18, and 19 connect to component input/output terminals 64 (FIGS. 4 and 5) of components 12 when such components are connected to the cartridge system 10. The manifold terminal to input/output terminal connections allow the flow of fluids out from the cartridge system 10 and into the component 12 and/or out from the component 12 and into the cartridge system 10. Switches 49 may be omitted if desired and fluid flow may be controlled by the pumps of devices attached to the inputs. For example, consider junction 55. If fluid is pumped into input 51 and static pressure is maintained at input 53, the junction 55 functions almost like a switch. Only fluid from input 51 passes to capillary plug in 24 and input 53 is functionally "switched off" with no switch involved.

Input/outputs 41, 43, and 45 may be used as reagent inputs. For example, input/outputs 41, 43, and 45 may all be connected at connection block terminal 54 (FIG. 1). Inputs 51 and 53 may be connection block terminals 50 and 52 respectively (FIG. 1). Furthermore, output 47 may be connection block terminal 56 (FIG. 1). In such an embodiment, two distinct reagents could be supplied to inputs 51 and 53 through connection block terminals 50 and 52 respectively (FIG. 1), a third distinct reagent could be supplied to input/outputs 41, 43, and 45 through connection block terminal 54 (FIG. 1), and the output 56 of the system could be received through connection block terminal 56 (FIG. 1).

In other embodiments, the switches 49 in fluidic junctions 57, 59, and 61 may be manipulated in order to remotely receive product from the system before progressing to the output 47. For example, the switch 49 of fluidic junction 61 may be manipulated such that the connection with capillary plug-in 28 is blocked. Input/output 45 may be connection block terminal 56 (FIG. 1), through which product may be received. It should be understood that numerous combinations of switch configurations and input/output scenarios are possible with such a cartridge system 10. Also, the flow of fluid may be controlled through junctions 57, 59 and 61 without switches by using pumps to create positive or negative pressure in the inputs and outputs, or to maintain a constant volume in an input or output. As used herein, the term switch references a small bore or microfluidic valve and the mechanisms used to activate and control the valve. Furthermore, fluid flow through the cartridge system may progress in either direction, that is, output 47 may receive a reagent for system input and inputs 51 and 53 may supply product.

Also, the various input/outputs may be configured to remotely flush particular components 12 with solvent for cleaning. Such remote cleaning may be configured by manipulation of the necessary switches 49 in the proper fluidic junctions 57, 59, and 61. As schematically illustrated, each of the capillary plug-ins, such as plug-in 24, may be provided with a cooling source 77 or a heat source 78. During a reaction in the plug-in 24, the plug-in and the reactants may be heated or cooled as desired. The number of connection block terminals 50, 52, 54, 56 (FIG. 1), the number of input/outputs 41, 43, and 45, and the number and nature of components 12 could increase, decrease, or change in various embodiments of the cartridge system 10. FIG. 3 represents only particular embodiments of the cartridge system 10 and is intended for illustrative purposes.

In addition to being connection block terminals 50, 52, 54, or 56, input/outputs 41, 43, and 45 may be remote input/outputs 66 as shown on the microfluidic circuit plug-in of FIG. 4 and the capillary plug-in of FIG. 5. Furthermore, input/outputs 41, 43, and 45 may be represented by nodes 40, 42, 44 and/or 46 on the trace surface 38 of the manifold 20 (shown on FIG. 2). Also, input/outputs 41, 43, and 45 may be both a remote input/output 66 on a component 12 and a connection block terminal 50, 52, 54, or 56. Such a configuration, or the configuration of other embodiments is represented on the cartridge system's trace surface 38 by traces and nodes such as trace 48 and nodes 40, 42, 44, and 46. It will be understood that the fluid from one output is typically connected to be an input to the next stage, (e.g. the next capillary plug-in).

FIG. 4 is a schematic diagram of a microfluidic circuit plug-in 30. Most glass microfluidic etched devices are constructed to resemble the microfluidic circuit plug-in 30 shown in FIG. 4. Unfortunately, the flat design is very costly because processes similar to silicon thin-film etching are used to detail the glass microfluidic circuits contained within the cartridge 65 of the microfluidic circuit plug-in 30. The diagram shows two component fastener apertures 62 used to attach the microfluidic circuit plug-in 30 to the manifold 20 of the cartridge system 10. The component fastener apertures 62 may be designed to accommodate screws or other types of fasteners. The manifold fastener apertures 36 are spaced in such a way to accommodate the attachment of several microfluidic components 12 to the manifold 20. Referring generally to any microfluidic component 12, attachment to the manifold 20 is accomplished, in one embodiment, by aligning the component fastener apertures 62 of the component device 12 with the manifold fastener apertures 36 of the manifold 20 as shown in FIGS. 1 and 2. The component 12 may then be secured to the manifold 20 by screw, peg, or other fastener.

Referring to FIG. 3, once the microfluidic circuit plug-in 30 is attached to the manifold 20 of the cartridge system 10, the component input/output terminals 64 should align and form a seal with ports in the lower surface 22 of the manifold 20. The circuit input/output terminals 64 provide an input and an output for fluids running through the cartridge system 10 to enter and to exit the microfluidic circuit plug-in 30. Remote input/outputs 66 are perpendicular to the component input/output terminals 64 and the component fastener apertures 62 of the base 68 of the microfluidic circuit plug-in 30. Component input/output terminals 64 perform the same function regardless of the type of component in which the terminals reside. They provide a connection between the ports on the lower surface 22 of the manifold 20 of the cartridge system 10 and the circuitry within the microfluidic component 12.

The component fluidic circuitry may consist of etched cartridge based glass circuitry such as that of a microfluidic circuit plug-in 30 or may consist of a spool of capillary tubing such as that of a capillary plug-in 24. The component input/output terminals 64 are recessed from the surface of the base so that a sealing device, such as a toroidal o-ring 94 (FIGS. 6 and 7), may be placed inside the terminals 64 between the base 68 of the component 12 and the ports on the lower side of the manifold 20. Remote input/outputs 66 are shown as vertical cylindrical apertures and are connected to the microfluidic circuitry at the same point as the component input/output terminals 64. The remote input/output terminals 66 perform the function of a fluidic tee junction, which is a junction in the fluidic circuit where fluid may be input from more than one source, which in this case would be from the component terminal 64 and the remote terminal 66. In one embodiment, each component terminal 64 and remote input/output 66 has a corresponding switch 67 for allowing or blocking flow into or out of the component terminal 64 and/or the remote input/output 66. The remote input/outputs 66 provide additional uses because they allow individual microfluidic components 12 to be remotely cleansed by flushing with cleaning fluids, in which case one remote input/output 66 would be used as an input for solvent or other cleansing fluid and the other remote input/output 66 would be used an output. In such a case, switches 49 (FIG. 3) are configured to block flow from the component terminals 64 but allow flow into one remote input/output 66 and flow out from the other remote input/output 66.

Referring now to FIG. 5, a diagram of a capillary plug-in 24, 26, or 28, is shown in greater detail. The capillary plug-ins may perform the function of fluidic reactors and support high speed chemistry and quick, low cost production. However capillary plug-ins may also perform the function of supplying reagent. The input and output of a horizontally wound coil such as the coil of the machined manifold cartridges 114 (shown in FIGS. 10-12), must be disposed in a plane perpendicular to the substantially parallel planes occupied by the coil or body portion of the fluidic tubing. Therefore, at least two bends must be present in horizontally wound coils: one at the front end before the input of the coil and one at the back end before the output of the coil.

Describing the vertical capillary plug-in shown on FIG. 5, the mounting block 70 of the capillary plug-in 24 has several cylindrical apertures through the entire mounting block 70. The component fastener apertures 62, the mounting aperture 72, and the component input/output terminals 64 are depicted as vertical holes through the entire mounting block 70 of the capillary plug-in 24. The component fastener apertures 62 perform a similar function as the component fastener apertures 62 of the microfluidic circuit plug-in 30. That is, they allow the component 12 to connect to the manifold 20 of the cartridge system 10 when coupled with a fastener such as a screw, peg, or other fastener.

Figure 6:
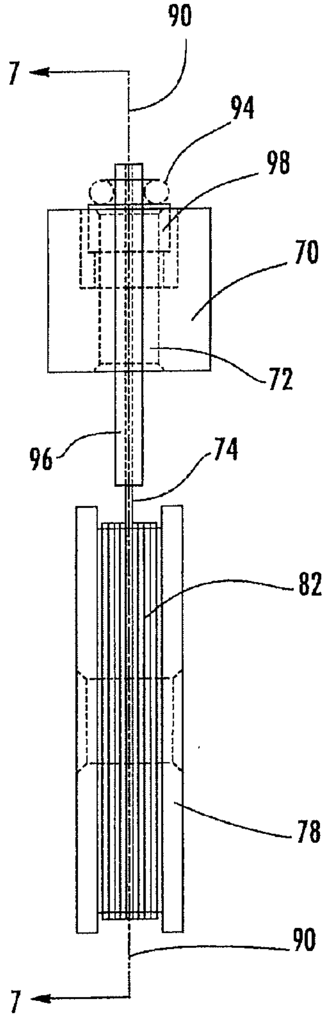
Figure 7:
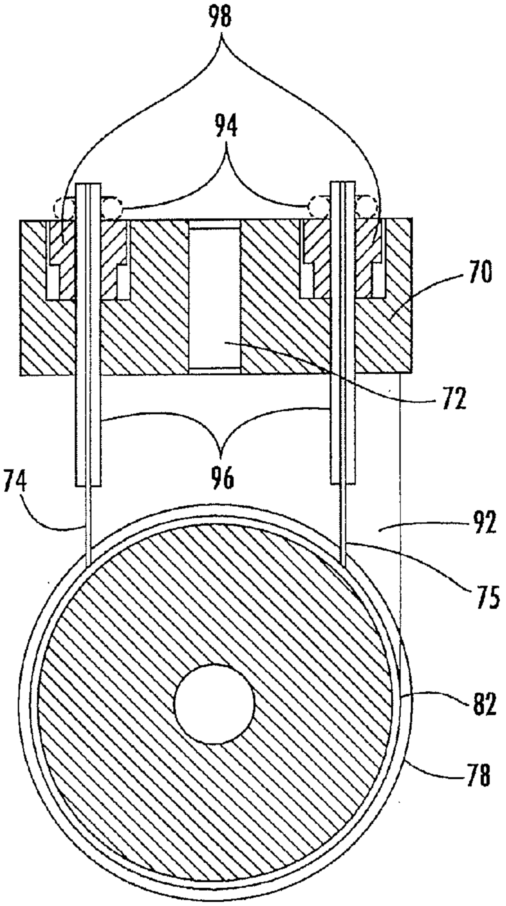

The component input/output terminals 64 allow for the placement of a sealing device such as, for example, a toroidal o-ring 94 (shown in FIGS. 6 and 7) or a Polyetheretherketone (PEEK) or Teflon compression seal 98 (shown in FIGS. 6, 7 and 9) (or a seal made from other materials) or a combination of both a toroidal o-ting 94 and a compression seal 98 (as shown in FIGS. 6 and 7) around the connection of the fluidic tubing transport portions 74 and 75 and the microfluidic component ports 134 (FIG. 11) of the manifold 20 of the cartridge system 10. The fluidic tubing transport portions 74 and 75 are connected to the coil 82 of fluidic tubing and are preferably lengths of tubing used to transport fluid from the component input/output terminals 64 to the body portion, preferably a coil 82. The fluidic tubing, in different embodiments, consists of glass, plastic, or other materials. Furthermore, fluidic tubing, in one embodiment, is small bore tubing with an inside diameter of about one to about twenty-five hundred micrometers, but other forms of fluid tubing may also be used. Preferably, the fluidic tubing is microfluidic tubing, which is microbore tubing with an inside diameter of about one to about five hundred micrometers.

In the preferred embodiment, the body portion of the fluidic tubing, preferably a coil 82, is of sufficient length to form a flow reactor. Such a flow reactor is capable of various functions including reacting multiple chemicals and applying reaction or external heat to such reactions. Heat may be applied or removed by an outside device connected, substantially surrounding, or disposed near the fluidic tubing. For example, a heat transfer device may be connected to the spool 78 (or to an external spool) in order to transfer heat through the spool and into the body portion or coil 78 of the fluidic tubing. Each end of the body portion or coil 82 is connected to a fluidic tubing transport portion 74 and 75, which go through the mounting block 70 of the capillary plug-in 24 and connect to the component input/output terminals 64. The coil 82 is preferably wound around a spool 78 in a manner similar to the way a garden hose may be kept on a holder. In other embodiments, however, the coil 82 need not be wound around anything, but rather may be supported by an epoxy protector 92 or epoxy fill 92 (shown in FIG. 7). In such case, the protector 92 would be considered the spool. In other embodiments, the spool may be external of the coil 82 or even lateral to the coil 82. The spool 78 and the coil 82 have a cylindrical aperture situated through the entire spool 78. In one embodiment, an L-bracket 76 is formed such that one side of the L-bracket 76 slides into a groove 84 on the outside of the spool 78 and may be attached by screw, peg, or other fastener through the spool aperture 80. The other side of the L-bracket 76 slides into a groove 86 on the underside of the mounting block 70 of the capillary plug-in 24 such that an aperture 88 in the L-bracket 76 corresponds to the mounting aperture 72 in the mounting block 70 and may be attached by screw, peg, or other fastener.

The remote input/outputs 66 located in the side of the mounting block 70 of the capillary plug-in 24 are situated perpendicular to the component input/output terminals 64. The remote input/outputs 66 perform the same function as those on microfluidic circuit plug-in 30, which is that of a fluidic tee junction, which, as described above, is a junction in the fluidic circuit where fluid may be input from more than one source or input and/or output for the purpose of remote cleaning. When the remote input/output 66 is used as an input, the two sources of fluid may be from a component input/output terminal 64 and the remote input/output 66. The remote terminals 66 also provides a way to remotely flush individual microfluidic components with cleansing fluids, and, as discussed above, the component terminals 64 serve as inputs and outputs to the cartridge system when a component 12 is connected to the cartridge system 10.

Referring to FIG. 6, a side view of the capillary plug-in 24, dotted line 90 shows the plane from which the cross-sectional view shown in FIG. 7 is taken. FIGS. 6 and 7 demonstrate another embodiment of the capillary plug-in 24, which does not utilize remote input/output terminals 64 as part of a fluidic tee junction as shown in the embodiment of FIG. 5. Also, the embodiment in FIGS. 6 and 7 utilizes an epoxy protector or fill 92 as opposed to an L-bracket 76 for securing the coil 82, the spool 78 and the fluidic tubing transport portions 74 and 75 to the mounting block 70 of the capillary plug-in 24. Using an epoxy protector 92 provides the benefit of protecting potentially breakable fluidic tubing that could be exposed in embodiments where epoxy protector 92 is not used. Furthermore, epoxy protector 92 is increasingly beneficial in embodiments where the fluidic tubing coil 82 is not wound around a spool 78.

Additionally, the embodiment of FIG. 6 utilizes a tubing sleeve 96 that surrounds the fluidic tubing transport portions 74 and 75 of capillary tubing. The purpose of the tubing sleeve 96 is to protect the fluidic tubing transport portions 74 and 75 and to aid in producing a seal between the mounting block 70 and the microfluidic component ports 134 (FIG. 11) on the lower surface 22 of the manifold 20. The seal is made as the capillary plug-in 24 mates with the manifold input/output terminals 136 (FIG. 11) of the microfluidic component port 134. The o-rings 94 are pushed down, compressing the compression fittings 98. The compression fittings 98 provide pressure on the o-rings 94, and therefore form a seal. In other embodiments, the seal may be formed by o-ring 94 without a compression fitting 98 or alternatively by a compression fitting 98 without an o-ring 94. Furthermore, this embodiment provides only one attachment mechanism, the mounting aperture 72 located in the middle of the mounting block 70, but other embodiments could use multiple mounting apertures and fasteners.

Figure 8:
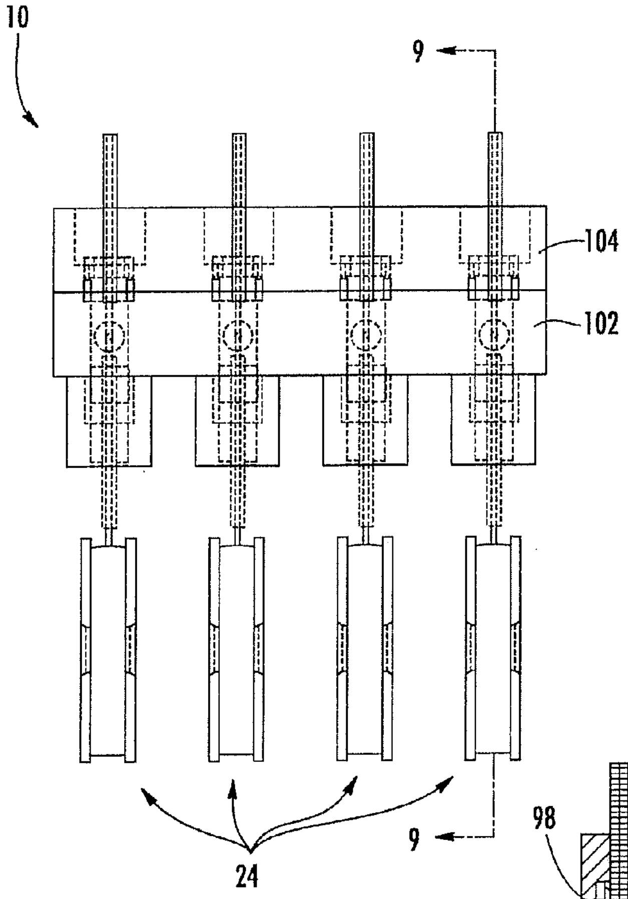
FIG. 8 is a side view of a cartridge system with four capillary plug-ins.
Figure 9:
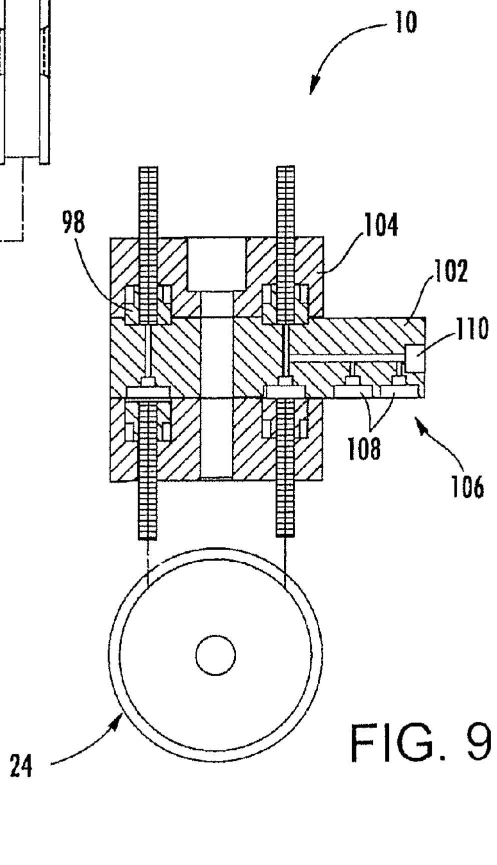

FIG. 8 shows another embodiment of the cartridge system 10. A side view of a group of four capillary plug-ins 24 connected to a fluid interface block 102, which is connected to a tubing connector block 104 is illustrated. The fluid interface block 102 is one embodiment of a manifold 20 (FIG. 1), that is, the manifold 20 may be a fluid interface block 102. The embodiment of FIG. 8 is a cartridge system 10 with several component devices, which are capillary plug-ins 24. Section line 9-9 defines the cross section shown in FIG. 9. As shown in FIG. 9, the fluid interface block 102 has a fluidic cross junction 106 consisting of two input terminals 108, one remote output terminal 110, and which is connected to one of the fluidic tubing transport portions 74 or 75 of the capillary plug-in 24. The fluidic cross junction 106 allows for the combining of two input fluids through the input terminals 108 and the remote cleansing of the capillary plug-in 24 through the remote output terminal 110. The fluid interface block 102 is also connected to the tubing connector block 104, which provides the opportunity to connect the fluidic system to other components 12, other cartridge systems 10, or outside systems not shown in the figures.

Figure 10:
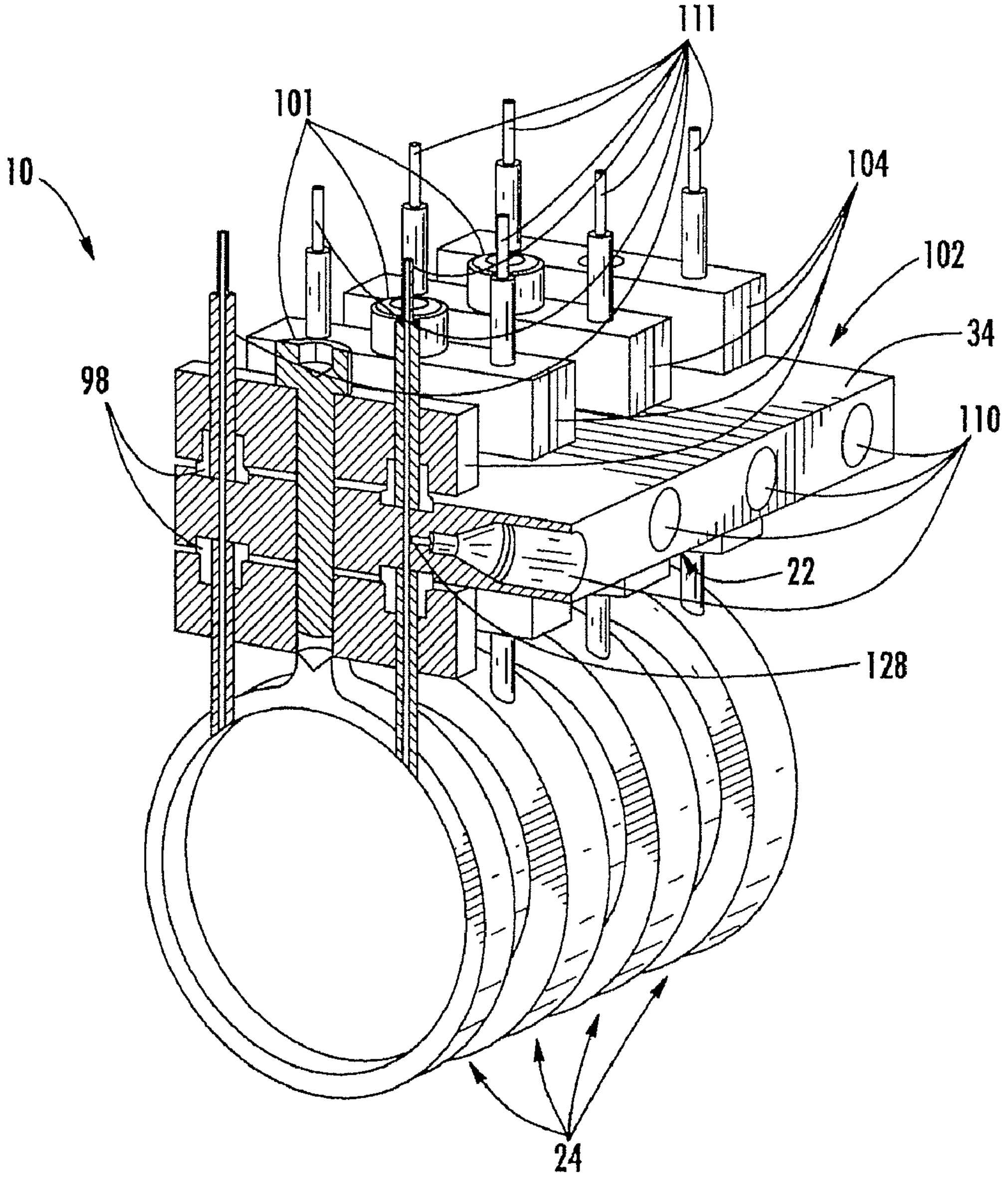
FIG. 10 is the cartridge system of FIGS. 8 and 9 including a fluid interface block and several capillary plug-ins.

Referring to FIG. 10, an embodiment of the cartridge system 10 shown in FIGS. 8 and 9 is shown with a cross section 9-9 (FIG. 8) removed from its front. As discussed above, the capillary plug-ins 24 engage the fluid interface block 102 on its lower surface 22. Furthermore, several tubing connector blocks 104 engage the fluid interface block 102 on its upper surface 34. The capillary plug-ins are attached to the fluid interface block 102 and the tubing connector blocks 104 by fasteners 101. In this embodiment, the tube is wound inside plug-in 24 such that the plug-in 24 may be regarded as a spool that is exterior of and lateral to the cost of tubing.

Figure 11:
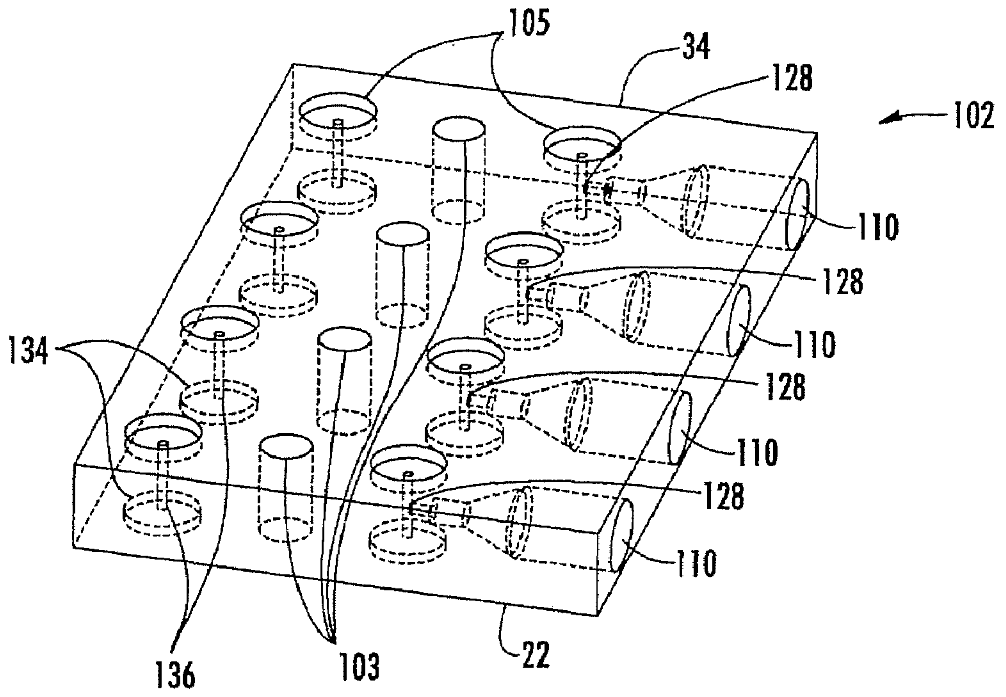
FIG. 11 is an illustration of a fluid interface block.

Referring to FIG. 11, the fluid interface block 102, which is one embodiment of a manifold 20 (FIG. 1) is shown. The capillary plug-ins 24 and the tubing connector blocks 104 are attached to the fluid interface block 102 by fasteners 101 as discussed regarding FIG. 10. The fasteners 101 pass through the fluid interface block 102 at fastener apertures 103. Connector block ports 105 are shown on the upper surface 34 of the fluid interface block 102. These ports are connected to the microfluidic component ports 134 on the lower surface 22 of the fluid interface block 102 by way of the fluid connector block throughways 136.

In this embodiment, input terminals 108 (FIG. 9) are not present but rather, the terminals 110, 111 and 113 may serve the function of the either input or output of fluids. The terminals 110 are also connected to some of the connector block throughways 136 at fluidic tee junctions 128 providing the opportunity for remote filling or flushing of the system. Also, note that the upper surface 34 of the fluid interface block 102 is similar to the lower surface 22, and therefore in other embodiments the upper surface 34 and the lower surface 22 are interchangeable. Consequently, in some embodiments, the connector block ports 105 are interchangeable with the microfluidic component ports 134.

Figure 12:
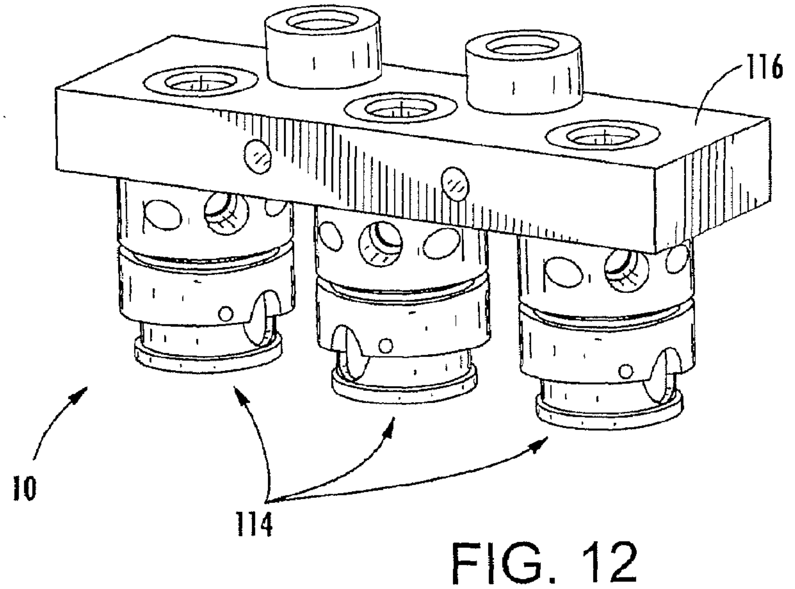
FIG. 12 is a cartridge system having a retaining block and three machined manifold cartridges.
Figure 13:
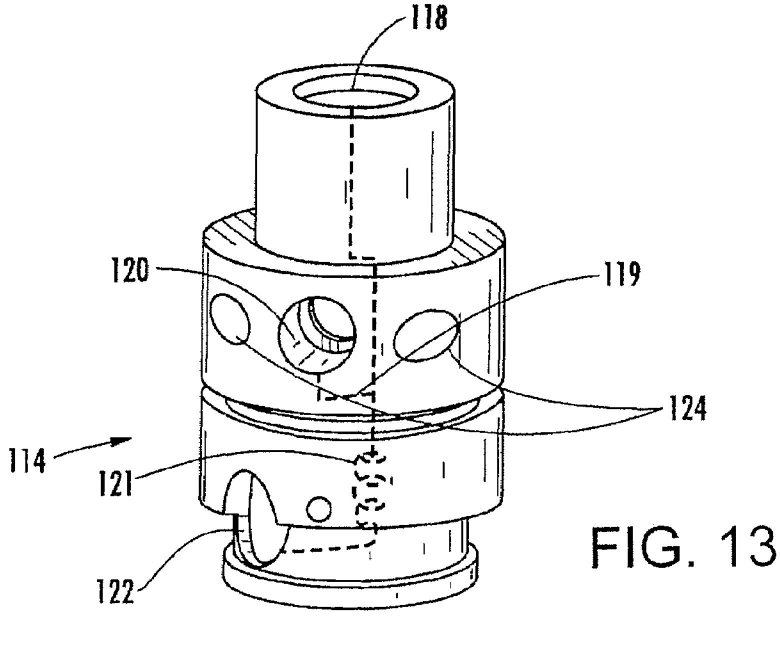
FIG. 13 is an enlarged view of a machined manifold cartridge.

Referring now to FIG. 12, another embodiment of the cartridge system 10 is shown. Several machined manifold cartridges 114 are mounted in a retaining block 116. FIG. 13 is a close-up of a machined manifold cartridge 114. In the preferred embodiment, the machined manifold cartridges 114 are constructed of plastic, contain two input ports 118 and 120, one for a first reagent 118 and one for a second reagent 120, a built-in fluidic junction (schematically represented at 119), a coil of capillary tubing wound horizontally (schematically represented by dashed line 121), and an output 122. The retaining block 116 of FIG. 12 serves as a mounting station for the machined manifold cartridges 114. However, the retaining block 116 does not serve the same purpose as the manifold 20 shown in FIGS. 1 and 11, because the functions of the manifold such as interior fluidic circuitry are substantially contained within the machined manifold cartridges 114 in the preferred embodiment. In this embodiment, the retaining block 116 serves more as an anchor for the machined manifold cartridges rather than an active participant in the fluidic circuitry. The machined manifold cartridges 114 also contain several tubing through holes 124 so that capillary tubing and thicker, input/output lines may be routed through the cartridges with ease.

The several embodiments detailed above demonstrate the modular and reconfigurable multi-stage microreactor cartridge apparatus and its numerous uses. The cartridge system 10 and the microfluidic components 12 described herein are capable of sustaining high temperatures of up to about 300 degrees Celsius and high pressures of up to about 5000 pounds per square inch. Such capabilities allow the microcartridge system 10 and components 12 to be used for extreme condition reactions not possible with other reaction mechanisms. Furthermore, other challenges associated with microfluidics include increasing the speed of microfluidic reaction processes and reducing the amount of dead space associated with microfluidic systems. The cartridge system design addresses these concerns through various embodiments, one of which utilizes an assembly of individual flow reactors attached to a manifold enabling quick, low dead-volume connections. The various embodiments also provide for remote removal of waste and input of reagents. Furthermore, the vertical winding found in the capillary plug-in reactors provides for low-cost and low failure reactors for the cartridge system.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A cartridge system comprising:

a. a manifold;

b. a plurality of terminals formed in the manifold for receiving fluid into the manifold or supplying fluid out of the manifold;

c. a plurality of small bore connection passageways extending between the terminals for carrying fluid to and from the terminals, the small bore connection passageways being configured and connected to receive fluid from one small bore component through a terminal and transfer the fluid to another terminal and into another small bore component;

d. a plurality of small bore components having small bore component passageways for connecting to the terminals, for supplying fluid to the terminals, and for receiving fluid from the terminals, the small bore connection passageways and the small bore component passageways each having an inside diameter of about one to about twenty-five hundred micrometers, wherein at least one of the plurality of small bore components comprises a cartridge comprising:

(i) a first transport portion for connecting to the terminals;

(ii) a second transport portion for connecting to the terminals; and (iii) a body portion substantially in the shape of a coil for connecting the first transport portion to the second transport portion, and (iv) a protector comprising a spool at least substantially encasing the body passageway portion of the component, the body portion being at least partially supported by an inside surface of the spool; and wherein the first transport portion is disposed along a first axis, the small bore tubing of the body portion is coiled around a second axis, and the second transport portion of the cartridge is disposed along a third axis, the first axis of the first transport portion and third axis of the second transport portion being substantially in parallel;

the second axis of the coil being substantially parallel to the plane of the manifold and not in parallel with the first axis and the third axis; and the first axis and the third axis being substantially perpendicular to a plane of the manifold;

e. the small bore components being configured for connection to the manifold with the small bore component passageways connected to transfer fluid to and from the terminals.

2. The cartridge system of claim 1 wherein the plurality of small bore connection passageways comprises microfluidic passageways having inner diameters of about one to about five hundred micrometers.

3. The cartridge system of claim 1 wherein the plurality of small bore component passageways comprises microfluidic passageways having inner diameters of about one to about five hundred micrometers.

4. The cartridge system of claim 1 wherein the plurality of small bore component passageways comprises small bore tubing.

5. The cartridge system of claim 1 wherein the plurality of small bore component passageways comprises microfluidic tubing having an inside diameter of about one to about five hundred micrometers.

6. The cartridge system of claim 1 wherein the plurality of small bore connection passageways comprises small bore tubing.

7. The cartridge system of claim 1 wherein the plurality of small bore connection passageways comprises microfluidic tubing having inner diameters of about one to about five hundred micrometers.

8. The cartridge system of claim 1 wherein the small bore connection passageways are formed in the manifold.

9. The cartridge system of claim 1 wherein at least one of the plurality of small bore components is a capillary plug-in having tubular passageways capable of withstanding pressure inside the tubular passageways up to 5000 psi.

10. The cartridge system of claim 1 wherein at least one of the plurality of small bore components is a microfluidic circuit plug-in and a source for providing at least one of heating or cooling to the plug-in.

11. The cartridge system of claim 1 further comprises at least one switch disposed for engaging at least one of the plurality of small bore connection passageways, the switch for interrupting a flow of the fluid passing though at least one passageway.

12. The cartridge system of claim 1 wherein at least two of the plurality of small bore connection passageways intersect at a fluidic junction.

13. A cartridge system comprising:

a manifold and a plurality of terminals formed in the manifold, a plurality of small bore components, each comprising:

a. a first transport passageway portion for connecting to the terminals;

b. a second transport passageway for connecting to the terminals;

c. a body passageway portion substantially in the shape of a coil for connecting the first transport portion to the second transport portion, the body passageway portion being formed at least in part by small bore tubing; and d. a protector at least substantially encasing the body passageway portion of the component, the body portion being at least partially supported by an inside surface of the protector;

wherein the first transport portion is disposed along a first axis, the small bore tubing of the body portion is coiled around a second axis, and the second transport portion of the cartridge is disposed along a third axis, the first axis of the first transport portion and third axis of the second transport portion being substantially in parallel;

the second axis of the coil being substantially parallel to the plane of the manifold and not in parallel with the first axis and the third axis; and the first axis and the third axis being substantially perpendicular to a plane of the manifold.

14. The cartridge system of claim 13 wherein the plurality of small bore component passageways comprises small bore tubing having an inner diameter of about one to about twenty-five hundred micrometers.

15. The cartridge system of claim 13 wherein the plurality of small bore passageways comprises microfluidic tubing having an inner diameter of about one to about five hundred micrometers.

16. The cartridge system of claim 13 wherein the plurality of small bore component passageways comprises glass tubing.

17. The cartridge system of claim 13 wherein the plurality of small bore component passageways comprises plastic tubing.

18. The cartridge system of claim 13, wherein the protector comprises a spool.

19. A cartridge system comprising:

a manifold and a plurality of terminals formed in the manifold, a plurality of components, each comprising:

a. a first transport passageway portion for connecting to the terminals;

b. a second transport passageway for connecting to the terminals;

c. a body passageway portion substantially in the shape of a coil for connecting the first transport portion to the second transport portion, the body passageway portion being formed at least in part by tubing; and d. a protector at least substantially encasing the body passageway portion of the component, the body portion being at least partially supported by an inside surface of the protector;

wherein the first transport portion is disposed along a first axis, the tubing of the body portion is coiled around a second axis, and the second transport portion of the cartridge is disposed along a third axis, the first axis of the first transport portion and third axis of the second transport portion being substantially in parallel;

the second axis of the coil being substantially parallel to the plane of the manifold and not in parallel with the first axis and the third axis; and the first axis and the third axis being substantially perpendicular to a plane of the manifold.

20. The cartridge system of claim 19 wherein the body passageway portion is a spool and a coil of small bore tubing supported by a surface of the spool.

21. The cartridge system of claim 19 wherein the plurality of small bore passageways comprises microfluidic tubing having an inner diameter of about one to about five hundred micrometers.

22. The cartridge system of claim 19, wherein the protector comprises a spool.

* * * * *

UNITED STATES PATENT AND TRADEMARK OFFICE

CERTIFICATE OF CORRECTION

PATENT NO. : 7,641,860 B2
APPLICATION NO. : 11/421678
DATED : January 5, 2010
INVENTOR(S) : Matteo It is certified that error appears in the above-identified patent and that said Letters Patent is hereby corrected as shown below:

Title page, col. 2, under (57) ABSTRACT, line 14, delete "would" and insert -- wound --.

Col. 11, claim 11, line 3, delete "though" and insert -- through --.

Signed and Sealed this

Sixteenth Day of March, 2010

David J. Kappos
*Director of the United States Patent and Trademark Office*